US011007319B2

(12) United States Patent
Malave et al.

(10) Patent No.: US 11,007,319 B2
(45) Date of Patent: May 18, 2021

(54) SYSTEMS AND METHODS FOR MANAGING DIABETES

(71) Applicants: Luis Malave, San Marcos, CA (US); Jesse Jaejin Kim, San Jose, CA (US)

(72) Inventors: Luis Malave, San Marcos, CA (US); Jesse Jaejin Kim, San Jose, CA (US)

(73) Assignee: EOFLOW INC., Seongnam (KR)

( * ) Notice: Subject to any disclaimer, the term of this patent is extended or adjusted under 35 U.S.C. 154(b) by 169 days.

(21) Appl. No.: 15/943,702

(22) Filed: Apr. 3, 2018

(65) Prior Publication Data

US 2019/0298917 A1 Oct. 3, 2019

(51) Int. Cl.
A61M 5/172 (2006.01)
A61M 5/142 (2006.01)
G16H 20/13 (2018.01)
H04L 29/06 (2006.01)

(52) U.S. Cl.
CPC ........ *A61M 5/172* (2013.01); *A61M 5/14248* (2013.01); *A61M 5/1723* (2013.01); *G16H 20/13* (2018.01); *H04L 63/0428* (2013.01); *A61M 2205/18* (2013.01); *A61M 2205/3553* (2013.01); *A61M 2205/3592* (2013.01); *A61M 2205/583* (2013.01); *A61M 2230/201* (2013.01)

(58) Field of Classification Search
CPC ................ A61M 5/172; A61M 5/1723; A61M 5/14248; A61M 2205/18; A61M 2205/3553; A61M 2230/201; A61M 2205/583; A61M 2205/3592; H04L 63/0428; G16H 20/13; G16H 40/20; H04W 12/00512; H04W 12/00503; H04W 12/001
See application file for complete search history.

(56) References Cited

U.S. PATENT DOCUMENTS

| | | | | |
|---|---|---|---|---|
| 2011/0257798 | A1* | 10/2011 | Ali | G06F 11/1662 700/282 |
| 2014/0288947 | A1* | 9/2014 | Simpson | G16H 20/40 705/2 |
| 2016/0082187 | A1* | 3/2016 | Schaible | A61B 5/14532 604/504 |
| 2017/0182248 | A1* | 6/2017 | Rosinko | A61M 5/14244 |
| 2017/0189614 | A1* | 7/2017 | Mazlish | G16H 20/17 |
| 2018/0150613 | A1* | 5/2018 | Bossi | G06Q 10/087 |
| 2018/0221636 | A1* | 8/2018 | Stein | A61N 1/325 |

OTHER PUBLICATIONS

Dbees Mobile Application, 2011, http://www.dbees.com/features.php?lng=gb#id_56 (Year: 2011).*

* cited by examiner

*Primary Examiner* — Bhisma Mehta
*Assistant Examiner* — Rachel T. Smith
(74) *Attorney, Agent, or Firm* — Patent Law Office PC; Bao Tran

(57) ABSTRACT

A method to dispense medication using one or more fillable medical dispensers by providing the medical dispenser with a first predetermined medication dosage sufficient for a first predetermined dispensing period, wherein the first dispensing period ends on a first repetitive day of the week for ease of remembrance by a user; providing the medical dispenser with a second predetermined medication dosage sufficient for a second predetermined dispensing period, wherein the dispensing period ends on a second repetitive day of the week for ease of remembrance; and installing the medical dispenser at least twice a week at a repetitive weekly replacement schedule.

20 Claims, 3 Drawing Sheets

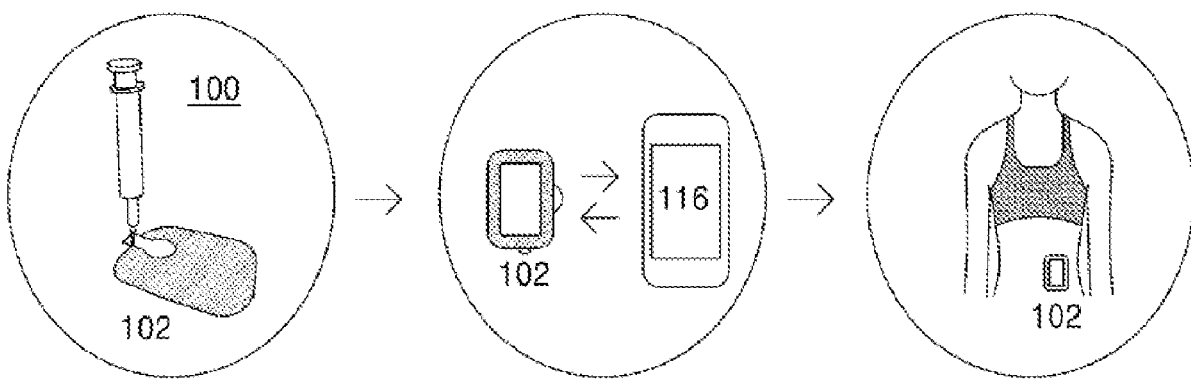

Provide the medical dispenser with a first predetermined medication dosage sufficient for a first predetermined dispensing period, wherein the first dispensing period ends on a first repetitive day of the week for ease of remembrance by a user (10)

↓

Provide the medical dispenser with a second predetermined medication dosage sufficient for a second predetermined dispensing period, wherein the dispensing period ends on a second repetitive day of the week for ease of remembrance (12)

↓

Install the medical dispenser at least twice a week at a repetitive weekly replacement schedule (14)

FIG. 1A

Communicate with the remote controller at the time of the change and setting an expiry time in the medical dispenser with the time set in the remote controller (20)

↓

Remote controller receives from the medical dispenser an alert to the user at a predetermined time prior to the expiry time (22)

↓

Disable the medical dispenser at an expiry time even if the remote controller is not near the patch or if contact with the remote controller is lost (24)

FIG. 1B

Encrypt communications between the remote controller and the medical dispenser (30)

↓

Encryption based on a patient identifier (32)

↓

Encryption based on EMEI (International Mobile Equipment Identity) (34)

FIG. 1C

Monitoring user with CGM (40)

↓

Automatically provide a bolus based on the CGM after losing contact with the remote controller for a predetermined period (42)

↓

Alternatively, confirm with the user before providing a bolus based on the CGM (44)

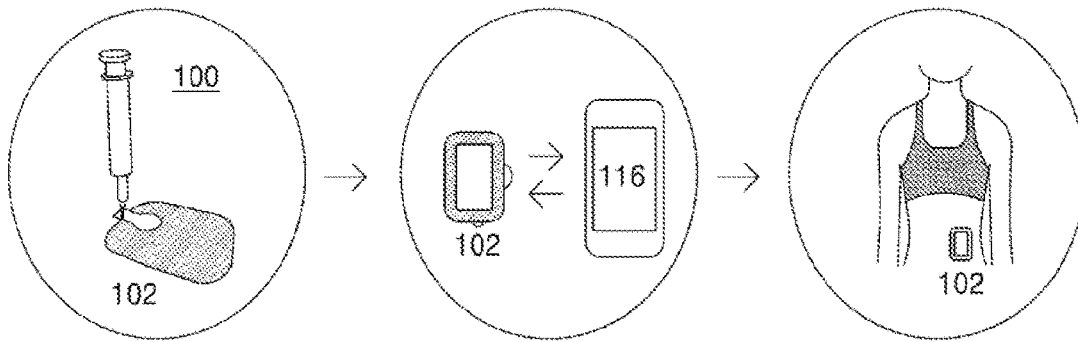

FIG. 3

| Provide the medical dispenser with a first predetermined medication dosage sufficient for a first predetermined dispensing period, wherein the first predetermined dispensing period ends on a first repetitive day of a week for ease of remembrance by a user |
| --- |
| Install the medical dispenser on the user on the first repetitive day |
| Provide the medical dispenser with a second predetermined medication dosage sufficient for a second predetermined dispensing period, wherein the dispensing period ends on a second repetitive day of the week for ease of remembrance |
| Install the medical dispenser on the user on the second repetitive day, wherein the medical dispenser is installed at least twice a week on a repetitive weekly replacement schedule, where a first dosage is sufficient for a first dispensing period, and a second dosage is sufficient for a second dispensing period. |

SYSTEMS AND METHODS FOR MANAGING DIABETES

BACKGROUND

The present application relates to disease management such as diabetes management.

Diabetes is a disease that can be managed by patients. The better the patient manages blood glucose level, the more likely he/she can prevent the host of complications that accompany the disease, such as eye damage or foot damage. Yet, the burden of constantly trying to manage blood sugar is sometimes too much for the patient.

For example, many wearable disposable insulin pump devices on the market today are designed to be worn for no more than 80 hours; usually intended for a three-days of usage or less, with some extra usage hours in case of emergency. With these systems, the changing cycle always varies; from Monday to Thursday to Sunday to Wednesday, etc. for example. Because of the lack of periodicity, users often forget when they need to change the wearable infusion device (patch), sometimes resulting in missing doses for an extended period of time, and therefore poor compliance.

SUMMARY

In one aspect, a method to dispense medication using one or more fillable medical dispensers by providing the medical dispenser with a first predetermined medication dosage sufficient for a first predetermined dispensing period, wherein the first dispensing period ends on a first repetitive day of the week for ease of remembrance by a user; providing the medical dispenser with a second predetermined medication dosage sufficient for a second predetermined dispensing period, wherein the dispensing period ends on a second repetitive day of the week for ease of remembrance; and installing the medical dispenser at least twice a week at a repetitive weekly replacement schedule.

Implementations of the above aspect can include one or more of the following. The system can have a first patch with a four day replacement cycle and a second patch having a three day replacement cycle, or vice versa. For example, a first patch can be used every Monday morning and a second patch every Thursday evening. Alternatively, the patches can be set up for use every Tuesday morning and every Friday evening, every Wednesday morning and every Saturday evening, every Thursday morning and every Sunday evening, every Friday morning and every Monday evening, every Saturday morning and every Tuesday evening, or every Sunday morning and every Wednesday evening, for example. The system can communicate with the controller at the time of the change and setting an expiry time in the patch with the time set in the controller. The patch can send an alert to the user at a predetermined time prior to the expiry time. The system can disable the patch at the expiry time even if the controller is not near the patch or the communication between the patch and the controller is lost. The system can render a bar graph, pie chart, or a pictorial presentation each representing a week with a pointer where a change interval is adjusted by sliding the pointer to position that represents the time of the week when the patch changes should occur. The system includes setting regular weekly change intervals where each of the intervals is below a predetermined time period, and can also include setting a patch from having the regular weekly change interval to a second predetermined time period.

In other implementations, the medical dispenser communicates with a remote controller such as a smart phone, among others. The method includes communicating with the remote controller at the time of the change and setting an expiry time in the medical dispenser with the time set in the remote controller. The remote controller can receive from the medical dispenser an alert to the user at a predetermined time prior to the expiry time. The system can disable the medical dispenser at an expiry time even if the remote controller is not near the patch or if contact with the remote controller is lost. The system can encrypt communications between the remote controller and the medical dispenser. The encryption of the communications between the remote controller and the medical dispenser can be based on a patient identifier or an IMEI (International Mobile Equipment Identity). The method includes providing Continuous Glucose Monitoring (CGM) of the user. The system can automatically provide a bolus based on the CGM after losing contact with the remote controller for a predetermined period. Alternatively, the system can confirm with the user before providing a bolus based on the CGM if a user glucose trend indicates a need for the bolus.

Advantages of the system may include one or more of the following. The system helps patients achieve high insulin compliance and can prevent complications arising from diabetes, such as blindness, kidney failures or loss of toes. High compliance is achieved because the system provides regularity in the patch changing intervals on weekly basis, such as, for examples, every Monday morning and Wednesday evening, or every Sunday morning at 9 am and Thursday morning at 7 am. This regularity can be achieved if the patch can be used for up to 4 days (or, to be more exact, 84 hours or longer) rather than for 80 hours. This way, for example, a device can be worn for four days, then the next one for three days, or every 84 hours such as every Saturday morning at 9 am and every Tuesday evening at 9 pm, and so on in order to maintain weekly regularity on the changing intervals. However, it is recommended by medical authorities such as Center for Disease Control that needles and/or cannulas be changed every 3 days in order to minimize any chance of developing infection on/around the infusion site of a user's body. Also, users may be tempted to use the device for the full four days every time in order to reduce the number of devices needed to be purchased or simply because of lack of attention. This will substantially increase the adverse chance of developing infection on the infusion area of the body. Thus, to comply with the professional recommendation as closely as possible and minimize the chance of developing infection while still maintaining a weekly regularity of changing terms, the pairing controller can limit the changing interval time. For example, the controller may be programmed to have a 'weekly regular replacement' feature that allows a user to preset the regular weekly change intervals such that each of the intervals is no more than, for example, 90 hours, while those devices not changed under this weekly regular replacement feature will be set to expire after three days or 80 hours, like many other wearable devices do today. The weekly regular replacement feature may include a bar graph, pie chart, or other pictorial presentations that each represents a week with a pointer such that the change interval can be adjusted by the sliding of the pointer to the position that represents the time of the week when the patch changes should occur.

Additionally, the wearable device (patch) can also be programmed so that it communicates with the controller at the time of the change and preset the time inside the patch firmware so that the patch expires at the same time set in the controller. This way, the patch can alert the user at predetermined time prior to the expiry time, and also shut down the patch at the expiry time even if a controller is not located near the patch or the communication between the patch and the controller is lost.

BRIEF DESCRIPTION OF THE DRAWINGS

In the drawings, like reference characters generally refer to the same parts throughout the different views. In the following description, various embodiments of the present invention are described with reference to the following drawings, in which:

FIGS. 1A-1D illustrate exemplary processes for managing insulin dispensing in the wearable automated medication delivery system.

FIG. 2 illustrates an exemplary wearable automated medication delivery system (medical dispenser).

FIG. 3 shows another exemplary process for managing insulin dispensing in the wearable automated medication delivery system.

DESCRIPTION

FIG. 1 shows an exemplary process to manage insulin replacement for an insulin device 102 (FIG. 2) which can be wearable device or a patch, among others. The process simplifies and regularizes the refill or replacement of the insulin delivery device 102 with an insulin capacity of less than a week. While the medical device insulin capacity can be increased to last exactly one week so that the refill or replacement always ends on a particular day of the week for ease of remembering, this is not preferred since medical professionals prefer that needles and/or cannulas be changed every 3 days in order to minimize any chance of developing infection on/around the infusion site of a user's body.

For users, it can be difficult to remember to refill or replace insulin dispensing devices on different days of the week. To help the user remember to refill or replace the insulin, the instant system splits the replacement or refill cycle into two or more events that occur on exactly the same days of the week so that users can easily remember when to replace or refill the device 102. Thus, to comply with the professional recommendation as closely as possible, to minimize the chance of developing infection, and to maintain regularity in replenishment events, a controller in the device 102 (FIG. 2) can apply the process of FIG. 1 in changing interval time. For example, the controller may be programmed to have a 'weekly regular replacement' feature that allows a user to preset the regular weekly change intervals such that each of the intervals is no more than, for example, 90 hours, while those devices not changed under this weekly regular replacement feature will be set to expire after three days or 80 hours, like many other wearable devices do today.

The weekly regular replacement feature may include a bar graph, pie chart, or other pictorial presentations that each represents a week with a pointer such that the change interval can be adjusted by the sliding of the pointer to the position that represents the time of the week when the patch changes should occur.

The refill or replacement cycle occurring on repetitive and specific day(s) of the week provides a consistency and ease of remembrance for the user. In one example, if the user changes the device 102 every Monday morning and every Thursday evening, it will become a natural weekly routine for users. Since the filling syringe can provide dosages for up to 4 days, the system ensures that the device 102 is refilled or replenished in a timely manner to ensure correct patient treatment.

The process of FIG. 1A includes the following:
Provide the medical dispenser with a first predetermined medication dosage sufficient for a first predetermined dispensing period, wherein the first predetermined dispensing period ends on a first repetitive day of the week for ease of remembrance by a user (10)
Provide the medical dispenser with a second predetermined medication dosage sufficient for a second predetermined dispensing period, wherein the second dispensing period ends on a second repetitive day of the week for ease of remembrance (12)
Install the medical dispenser at least twice a week at a repetitive weekly replacement schedule (14)

Additionally, the wearable device (patch) can also be programmed so that it communicates with the controller at the time of the change and preset the time inside the patch firmware so that the patch expires at the same time set in the controller. This way, the patch can alert the user at predetermined time prior to the expiry time, and also shut down the device/patch at the expiry time even if a controller is not located near the device. This process is illustrated in FIG. 1B as follows:
Communicate with the remote controller at the time of the change and setting an expiry time in the medical dispenser with the time set in the remote controller (20)
Remote controller receives from the medical dispenser an alert to the user at a predetermined time prior to the expiry time (22)
Disable the medical dispenser at an expiry time even if the remote controller is not near the patch or if contact with the remote controller is lost (24)

In operation 24, the device 102 is programmed to automatically turn off after a set interval by the user, for example after 24 hours of no connectivity with the remote controller. In that case, the device 102 will shut off for safety reasons if there are no communications for any reason.

In one embodiment, to provide enhanced security in the communications between the controller and the device 102, one embodiment uses a unique encryption between a particular phone by pairing the phone's unique number such as an IMEI (International Mobile Equipment Identity) number with the dispensing device 102. The user can find the IMEI by entering *#06# on the phone's call screen. You can also find it in your phone's settings or by inspecting the back of your phone, or underneath your phone's battery, or in the phone settings tab. In this embodiment, the device 102 would only accept commands from a phone with a matching IMEI number. This process is shown in FIG. 1C as follows:
Encrypt communications between the remote controller and the medical dispenser (30)
Encryption based on a patient identifier (32)
Encryption based on EMEI (International Mobile Equipment Identity) (34)

In the alternative of step 34, the device 102 is encrypted with a unique id that belongs to a particular patient number, and the app would transmit messages encrypted with the unique patient ID to ensure that the app is securely communicating with the right device with the right commands.

In another embodiment, the device 102 provides an automatic bolus depending on patient history or rapid Continuous Glucose Monitors (CGMs) uptick. CGMs monitor the body's glucose levels in real-time by sensing the glucose present in tissue fluid (also called interstitial fluid). Whereas a meter provides a measurement of the blood glucose at a specific moment in time, the CGM provides an overview of the blood glucose levels over a period of time. Based on the CGM trend, the device 102 can warn users if they are trending towards hypo- or hyperglycemia. They are particularly useful at night, as they can sound an alert if glucose levels drop. CGMs may need to be calibrated with a finger-stick blood sugar reading for optimal sensor accuracy. In one exemplary operation, if a time lapse exceeds 12-16 hours and the patient has forgotten or lost communication with the controller, the device 102 provides an additional bolus after confirming with the user. In other embodiments, the bolus can be provided automatically to the user, and a warning can be sent to caregivers of the user or medical professionals caring for the user. One implementation is shown in FIG. 1D as follows:

Monitoring user with CGM (40)
Automatically provide a bolus based on the CGM after losing contact with the remote controller for a predetermined period (42)
Alternatively, confirm with the user before providing a bolus based on the CGM (44)

FIG. 2 illustrates an exemplary dispensing device which can be a wearable disposable insulin pump or patch as a wearable automated medication delivery system 100. To use the device of FIG. 2, the user first applies a filling syringe found in a pump packet to fill patch or medical device 102 with insulin. Next, the user follows instructions provided on the paired controller to activate a new Patch 102. The user can then apply the new patch 102. The wearable automated medication delivery system 100 can include a medical device 102. The medical device 102 can be attached to the body of a user and can deliver a medication to the user. The medical device 102 can be a wearable device. In particular, the medical device 102 can be directly coupled to a user (e.g., directly attached to a body part and/or skin of the user). A surface of the medical device 102 can include an adhesive to facilitate attachment to the user. The medical device 102 can include a number of components to facilitate automated delivery of a medication to the user. For example, the medical device 102 can include a reservoir for storing the medication, a needle or cannula for delivering the medication into the body of the person, and a pump for transferring the medication from the reservoir, through the needle or cannula, into the body of the user. The medical device 102 can also include a power source such as a battery for supplying power to the pump and/or other components of the medical device 102. The medical device 102 can store and provide any medication or drug to the user. In various embodiments, the medical device 102 can be an automated wearable insulin delivery device. For example, the medical device 102 can be the EOPatch wearable insulin pump system, with the thin and light disposable pump unit (Patch), and the smart-phone like color touchscreen controller together with the advanced managing software tools, is designed to reduce the burden of insulin management, and make the user's life a little bit easier.

In general, the system can automatically monitor glucose levels of the user, automatically determine a delivery of insulin to the user based on the monitored glucose levels, and automatically provide the determined amount of insulin to the user. Each of these steps can be performed without any user input or interaction. In various embodiments, a user confirmation can be required before the insulin is provided to the user as discussed above. For example, when handheld electronic computing device 116 is implemented as a cellphone, for added security, the user can be required to confirm or acknowledge the determined delivery of insulin to the user. Without receiving such confirmation, the delivery can be blocked or prevented. This security feature can mitigate hacking or other cybersecurity risks.

As discussed above, the wearable insulin delivery device 102 can include one or more user output devices that can be used to provide an alarm, alert, notification, or indication to the user that an instruction for insulin delivery has been determined or received. This indication can be audible, visual, and/or vibrational for example. In various embodiments, the indication can include one or more flashing light emitting diodes and/or a vibration provided by the wearable insulin delivery device 102. One or more user input devices provided with the wearable insulin delivery device 102 can be used to provide a required confirmation from the user. The input devices can include a button, a touch screen, or an accelerometer (e.g., such that the input can be a tapping or movement of the wearable insulin delivery device 102). Although user input may be needed to ensure the final step of providing the determined level of insulin to the user occurs, such embodiments can be considered as largely automatic with one or more added security features for the user.

The medical device 102 can also contain analog and/or digital circuitry for controlling the delivery of the medication. The circuitry can be implemented as a controller. The circuitry can include discrete, specialized logic and/or components, an application-specific integrated circuit, a microcontroller or processor that executes software instructions, firmware, or any combination thereof. In various embodiments, the control circuitry can be configured to cause the pump to deliver doses of the medication to the person at predetermined intervals. The size and/or timing of the doses may be programmed into the control circuitry using a wired or wireless link by the user or by a third party (such as a health care provider).

Instructions for determining the delivery of the medication to the user (e.g., the size and/or timing of any doses of the medication) can originate locally (e.g., based on determinations made by the medical device 102) or can originate remotely and then provided to the medical device 102. Remote instructions can be provided to the medical device 102 over a wired or wireless link. The medical device 102 can execute any received instructions for the delivery of the medication to the user. In this way, under either scenario, the delivery of the medication to the user can be automated.

In various embodiments, the medical device 102 can communicate via a wireless link 104 with an electronic device 116. The electronic device 116 can be any electronic device such as, for example, an Apple Watch. The electronic device 116 can be a wearable wireless accessory device or can be a smart phone, among others. The wireless link 104 can be any type of wireless link provided by any known wireless standard. As an example, the wireless link can provide communications based on Bluetooth, Wi-Fi, a near-field communication standard, a cellular standard, or any other wireless protocol. The control circuitry in the medical device 102 may include circuitry implementing a wireless transmitter, receiver, and/or transceiver for communication over the link 104 or 122. Information may be transmitted between the medical device 102 and the electronic device 116 over the link 104 and/or between the medical device 102 over the link 122. The shared information may include handshake/pairing information, data, commands, status information, or any other such information.

In various embodiments, the electronic device 116 transmits a command to the medical device 102 that specifies an action for the medical device 102 to take regarding delivery of the medication. In another embodiment, the sensor sends a signal to the medical device 102 via the link 122, and the medical device 102 executes an algorithm to determine an action for the medical device 102 to take regarding delivery of the medication. The action may be delivery of a bolus of the medication, a change in a time, frequency, or schedule of future deliveries of the medication, a change in a size of future deliveries of the medication, or any other such action. The command may further comprise a bolus size, a bolus time, or any other such additional information. The medical device 102 may transmit a confirmation message back to the electronic device 116 upon receipt of the command and/or after completion of the action.

In various embodiments, the electronic device 116 transmits the command as specified by an algorithm executing thereon, such as an insulin bolus injection algorithm. The algorithm may execute in the context of a software application running on the electronic device. The user may download this application from an application store, such as the Apple iTunes store, or from any other source. The algorithm may be used to compute appropriate times and doses of delivery of the medication. In some embodiments, the algorithm bases these computations at least in part on information known about the person, such as sex, age, weight, or height, and/or on information gathered about a physical attribute or condition of the person (e.g., from the sensor). For example, the algorithm may determine an appropriate delivery of the medication based on glucose level monitoring of the user. The software application may further permit the person to access status information regarding the medical device 102, such as its battery level, number of doses remaining, amount of time in use, or other such status information. The software application may instead or in addition allow the person to issue commands to the medical device 102, such as a command to deliver a bolus.

In various embodiments, a sensor is worn on the body of the person or implanted within the person and is used to collect information regarding one or more physical attributes or conditions of the person. The sensor can be coupled to the user and worn on a body part of the user. The sensor can be a glucose sensor. For example, the sensor can be a continuous glucose monitor (CGM). Although the sensor is depicted as separate from the medical device 102, in various embodiments, the sensor and medical device 102 may be incorporated into the same unit. That is, in various embodiments, the sensor can be a part of the medical device 102 and contained within the same housing of the medical device 102 (e.g., the sensor can be positioned within or embedded within the medical device).

The sensor can include one or more sensing elements, an electronic transmitter, receiver, and/or transceiver for communicating with the electronic device 116 over a wired/wireless link or with medical device 102 over the link. The sensor can also include a power source for supplying power to the sensing elements and/or transceiver. Communications provided by the sensor may include data gathered from the sensing elements. This data can be transmitted continually, at periodic intervals, and/or during or after a change in sensed data (e.g., if a glucose level or rate of change in the level exceeds a threshold). The software application executing the algorithm may use this collected information to send a command to the medical device 102 to, for example, deliver a bolus to the person, change the amount or timing of future doses, or other commands.

The electronic device 116 can be considered to be a wireless accessory device or an intermediate device. In various embodiments, the electronic device 116 can relay commands for delivery of a medication from a remote source to the medical device 102. In various embodiments, the electronic device 116 can include a controller for determining delivery of the medication (e.g., the electronic device can include a controller for executing an "artificial pancreas" algorithm). The sensor can be any type of sensor and is not limited to a CGM. The sensor can include one or more sensors housed in the same physical unit.

The electronic device 116 and/or the medical device 102 may communicate with one more remote devices, which may include computers, servers, storage devices, cloud-based services, or other similar devices. The remote device may be owned or operated by, for example, health-care companies or services, pharmacies, doctors, nurses, or other such medically-related entities. The remote device may include a cloud-based data management system. A user may wish, for example, to back up data collected from the sensor, back up a record of medication delivery times and doses provided by the medical device 102, or back up other such information. A wireless link may be used to connect the electronic device 116 to the remote devices and/or a wireless link may be used to connect the medical device 102 to the remote devices.

Alternatively or in addition thereto, the electronic device 116 may communicate with a local device. The local device can be a dedicated control or monitoring device (e.g., a diabetes management device and/or a custom handheld electronic computing device), cellular phone, laptop computer, tablet, desktop computer, or other similar electronic computing device. The local device can communicate with the electronic device 116 over a wireless link. The wireless link can be of the same type as the other wireless links described herein.

A software application executing on the local device may be used to send commands to the medical device 102 (e.g., via the electronic device) and/or receive status information about the medical device 102 (e.g., via the electronic device). In other embodiments, the local device instead or in addition communicates directly via a wireless link with the medical device 102. Additionally, the sensor may communicate via a wireless link with the local device. The local device may communicate with the remote devices via a wireless link.

In general, the system 100 can automatically monitor glucose levels of the user, automatically determine a delivery of insulin to the user based on the monitored glucose levels, and automatically provide the determined amount of insulin to the user. Each of these steps can be performed without any user input or interaction. In various embodiments, a user confirmation can be required before the insulin is provided to the user as discussed above. For example, when handheld electronic computing device 102 is implemented as a cellphone, for added security, the user can be required to confirm or acknowledge the determined delivery of insulin to the user. Without receiving such confirmation, the delivery can be blocked or prevented. This security feature can mitigate hacking or other cybersecurity risks. Additionally, the wearable device (patch) can also be programmed so that it communicates with the controller at the time of the change and preset the time inside the patch firmware so that the patch expires at the same time set in the controller. This way, the patch can alert the user at predetermined time prior to the expiry time, and also shut down the patch at the expiry time even if a controller is not located near the patch or the communication between the patch and the controller is lost.

The system helps patients achieve high insulin compliance and can prevent complications arising from diabetes, such as blindness, kidney failures or loss of toes. High compliance is achieved because the system provides regularity in the patch changing intervals on weekly basis, such as, for examples, every Monday morning and Wednesday evening, or every Sunday morning at 9 am and Thursday morning at 7 am. This regularity can be achieved if the patch can be used for up to 4 days (or, to be more exact, 84 hours or longer) rather than for 80 hours. This way, for example, a device can be worn for four days, then the next one for three days, or every 84 hours such as every Saturday morning at 9 am and every Tuesday evening at 9 pm, and so on in order to maintain weekly regularity on the changing intervals. However, it is recommended by medical authorities such as Center for Disease Control that needles and/or cannulas be changed every 3 days in order to minimize any chance of developing infection on/around the infusion site of a user's body. Also, users may be tempted to use the device for the full four days every time in order to reduce the number of devices needed to be purchased or simply because of lack of attention. This will substantially increase the adverse chance of developing infection on the infusion area of the body. So to comply with the professional recommendation as closely as possible and minimize the chance of developing infection while still maintaining a weekly regularity of changing terms, the pairing controller can limit the changing interval time. For example, the controller may be programmed to have a 'weekly regular replacement' feature that allows a user to preset the regular weekly change intervals such that each of the intervals is no more than, for example, 90 hours, while those devices not changed under this weekly regular replacement feature will be set to expire after three days or 80 hours, like many other wearable devices do today. The weekly regular replacement feature may include a bar graph, pie chart, or other pictorial presentations that each represents a week with a pointer such that the change interval can be adjusted by the sliding of the pointer to the position that represents the time of the week when the patch changes should occur.

As discussed above, the wearable insulin delivery device 102 can include one or more user output devices that can be used to provide an alarm, alert, notification, or indication to the user that an instruction for insulin delivery has been determined or received. This indication can be audible, visual, and/or vibrational for example. In various embodiments, the indication can include one or more flashing light emitting diodes and/or a vibration provided by the wearable insulin delivery device 102. One or more user input devices provided with the wearable insulin delivery device 102 can be used to provide a required confirmation from the user. The input devices can include a button, a touch screen, or an accelerometer (e.g., such that the input can be a tapping or movement of the wearable insulin delivery device 102). Although user input may be needed to ensure the final step of providing the determined level of insulin to the user occurs, such embodiments can be considered as largely automatic with one or more added security features for the user.

Various embodiments include systems and methods for delivering a medication to a person using a wearable medical device in accordance with a wireless signal received from an electronic device. In various embodiments, the electronic device is a smart watch, smart necklace, module attached to the medical device, or any other type or sort of electronic device that may be worn or carried on the body of the person and executes an algorithm that computes the times and dosages of delivery of the medication. For example, the electronic device may execute an artificial-pancreas algorithm that computes the times and dosages of delivery of insulin. The electronic device may also be in communication with a sensor, such as a glucose sensor, that collects data on a physical attribute or condition of the person, such as a glucose level. The sensor may be disposed in or on the body of the person and may be part of the medical device or may be a separate device. Alternately, the medical device may be in communication with the sensor in lieu of or in addition to the communication between the sensor and the electronic device. The communication may be direct (if, e.g., the sensor is integrated with or otherwise a part of the medical device) or remote/wireless (if, e.g., the sensor is disposed in a different housing than the medical device). In these embodiments, the sensor and/or medical device contains computing hardware (e.g., a processor, memory, firmware, etc.) that executes some or all of the algorithm that computes the times and dosages of delivery of the medication.

Various embodiments described herein include systems and methods for automatically delivering medication to a user. A sensor coupled to a user can collect information regarding the user. A controller can use the collected information to determine an amount of medication to provide the user. The controller can instruct a drug delivery device to dispense the medication to the user. The drug delivery device can be a wearable insulin pump that is directly coupled to the user. The controller can be part of or implemented in a cellphone. A user can be required to provide a confirmation input to allow a determined amount of insulin to be provided to the user based on detected glucose levels of the user.

Certain embodiments of the present invention were described above. It is, however, expressly noted that the present invention is not limited to those embodiments, but rather the intention is that additions and modifications to what was expressly described herein are also included within the scope of the invention. Moreover, it is to be understood that the features of the various embodiments described herein were not mutually exclusive and can exist in various combinations and permutations, even if such combinations or permutations were not made express herein, without departing from the spirit and scope of the invention. In fact, variations, modifications, and other implementations of what was described herein will occur to those of ordinary skill in the art without departing from the spirit and the scope of the invention. As such, the invention is not to be defined only by the preceding illustrative description. Further, many of the techniques and embodiments described are not limited to the delivery of insulin but are applicable to the automated delivery of any medication to a user.

What is claimed is:

1. A method to dispense medication using a medical dispenser with a refillable reservoir, comprising the steps of:
    (a) filling the refillable reservoir in the medical dispenser with a first predetermined medication dosage sufficient for a first predetermined dispensing period, wherein the first predetermined dispensing period ends on a first repetitive day of a week selected for ease of remembrance by a user and attaching the medical dispenser to user skin;
    (b) on the first repetitive day, removing from the user skin and refilling the medical dispenser with a second predetermined medication dosage sufficient for a second predetermined dispensing period, wherein the second dispensing period ends on a second repetitive day of the week for ease of remembrance and attaching the medical dispenser on the user for use until the second repetitive day, and repeating steps a and b each week, wherein the medical dispenser is refilled and installed on a repetitive twice-a-week replacement schedule on the first and second repetitive days of the week and wherein the first and second repetitive days of the week are programmed by the user into a remote controller that communicates with the medical dispenser such that the user presets the first dispensing period to be no longer than 80 hours and the second dispensing period to be no longer than 90 hours, wherein the remote controller limits the first and second dispensing periods such that the first and second dispensing periods are not longer than the respective 80 and 90 hours.

2. The method of claim 1, wherein the first predetermined dispensing period comprises four days and the second predetermined dispensing period comprises three days.

3. The method of claim 1, wherein the first predetermined dispensing period comprises three days and the second predetermined dispensing period comprises four days.

4. The method of claim 1, comprising installing the medical dispenser every Monday morning and every Thursday evening.

5. The method of claim 1, comprising installing the medical dispenser every Tuesday morning and every Friday evening.

6. The method of claim 1, comprising installing the medical dispenser every Wednesday morning and every Saturday evening.

7. The method of claim 1, comprising installing the medical dispenser every Thursday morning and every Sunday evening.

8. The method of claim 1, comprising installing the medical dispenser every Friday morning and every Monday evening.

9. The method of claim 1, comprising installing the medical dispenser every Saturday morning and every Tuesday evening.

10. The method of claim 1, further comprising:
displaying on a mobile device a bar graph, pie chart, or a pictorial presentation representing one week with a user interface element.

11. The method of claim 1, wherein the remote controller comprises a smart phone.

12. The method of claim 1, comprising setting an expiry time in the medical dispenser with the time set in the remote controller.

13. The method of claim 12, comprising receiving from the medical dispenser an alert to the user at a predetermined time prior to the expiry time.

14. The method of claim 1, comprising disabling the medical dispenser at an expiry time even if the remote controller is not near the medical dispenser device or if contact with the remote controller is lost.

15. The method of claim 1, comprising encrypting communications between the remote controller and the medical dispenser.

16. The method of claim 1, comprising encrypting communications between the remote controller and the medical dispenser based on a patient identifier or an IMEI (International Mobile Equipment Identity).

17. The method of claim 1, comprising providing Continuous Glucose Monitoring (CGM) of the user.

18. The method of claim 17, comprising automatically providing a bolus based on the CGM after losing contact with the remote controller for a predetermined period.

19. The method of claim 17, comprising confirming with the user before providing a bolus based on the CGM if a user glucose trend indicates a need for the bolus.

20. A method to dispense medication using a medical dispenser with a refillable reservoir, comprising the steps of:
(a) filling the refillable reservoir in the medical dispenser with a first predetermined medication dosage sufficient for a first predetermined dispensing period, wherein the first predetermined dispensing period ends on a first repetitive day of a week selected for ease of remembrance by a user and attaching the medical dispenser to user skin;
(b) on the first repetitive day, removing from the user skin and refilling the medical dispenser with a second predetermined medication dosage sufficient for a second predetermined dispensing period, wherein the second dispensing period ends on a second repetitive day of the week for ease of remembrance and attaching the medical dispenser on the user for use until the second repetitive day, and repeating steps a and b each week, wherein the medical dispenser is refilled and installed on a repetitive twice-a-week replacement schedule on the first and second repetitive days of the week and wherein the first and second repetitive days of the week are programmed by the user into a remote controller that communicates with the medical dispenser such that the user presets the first dispensing period to be no longer than 90 hours and the second dispensing period to be no longer than 80 hours, wherein the remote controller limits the first and second dispensing periods such that the first and second dispensing periods are not longer than the respective 90 and 80 hours.

* * * * *